United States Patent

Melzer et al.

[19]

[11] Patent Number: 4,985,030
[45] Date of Patent: Jan. 15, 1991

[54] BIPOLAR COAGULATION INSTRUMENT

[75] Inventors: Andreas Melzer, Wiesbaden; Markus Naruhn, Lindlar; Karl Kipfmüller, Taunusstein; H. D. Reidenbach, Neunkirchen-Seelscheid; Gerd Buess, Nieder-Olm, all of Fed. Rep. of Germany

[73] Assignee: Richard Wolf GmbH, KniHingen, Fed. Rep. of Germany

[21] Appl. No.: 511,476

[22] Filed: Apr. 18, 1990

[30] Foreign Application Priority Data

May 27, 1989 [DE] Fed. Rep. of Germany ....... 3917328

[51] Int. Cl.$^5$ ............................................. A61B 17/39
[52] U.S. Cl. ............................................................. 606/51
[58] Field of Search ..................................... 606/51, 52

[56] References Cited

U.S. PATENT DOCUMENTS

| | | | |
|---|---|---|---|
| 1,714,220 | 5/1929 | Groff | 606/51 |
| 4,512,343 | 4/1985 | Falk et al. | 606/52 |
| 4,732,149 | 3/1988 | Sutter | 606/52 |
| 4,819,633 | 4/1989 | Bauer et al. | 606/52 |

FOREIGN PATENT DOCUMENTS

| | | | |
|---|---|---|---|
| 2324658 | 12/1974 | Fed. Rep. of Germany | 606/51 |
| 2355521 | 1/1978 | France | 606/52 |
| 0578972 | 11/1977 | U.S.S.R. | 606/51 |

*Primary Examiner*—Lee S. Cohen
*Assistant Examiner*—K. M. Pfaffle
*Attorney, Agent, or Firm*—Panitch, Schwarze, Jacobs & Nadel

[57] ABSTRACT

The bipolar coagulating instrument has an outer barrel whose distal end is provided with two halves of a first jaw member, said halves being angled relative to the longitudinal axis and being spaced apart from one another. An inner barrel is similarly provided with a second jaw member, which also has halves obliquely angled relative to the longitudinal axis and spaced apart from one another. The second jaw member is axially displaceable towards the first jaw member.

At least one of the two jaw members has recesses which are connected to a distally open end of an irrigation passage in the inner barrel. A cutting forceps or the like can be passed through a channel in the inner barrel and through the gap between the two sets of jaw member halves.

3 Claims, 2 Drawing Sheets

U.S. Patent   Jan. 15, 1991   Sheet 1 of 2   4,985,030
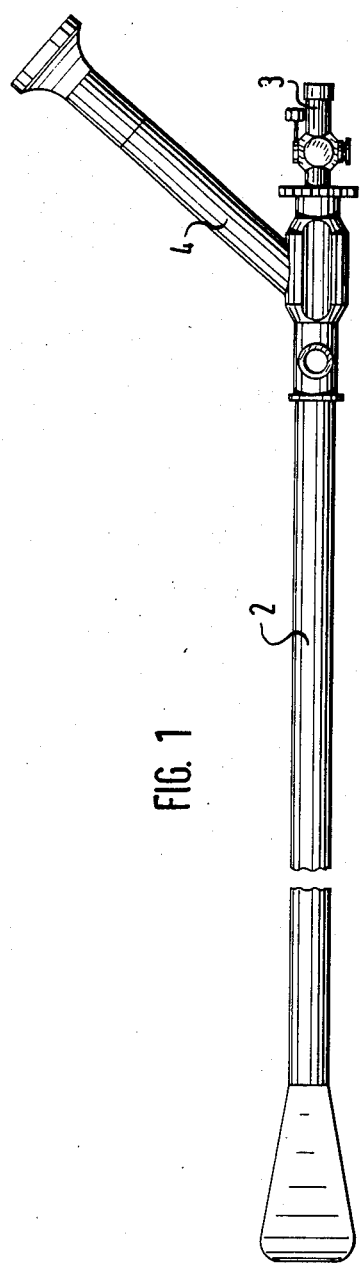
FIG. 1
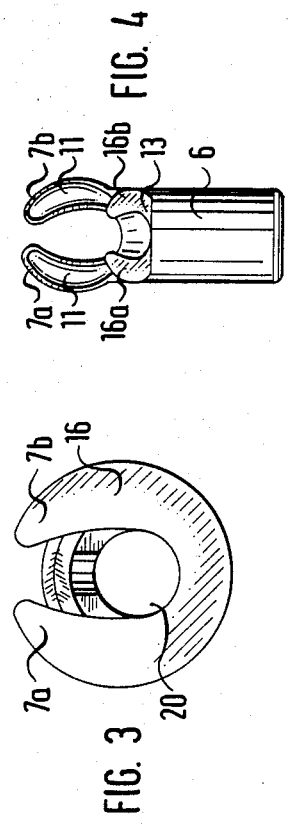
FIG. 4
FIG. 3
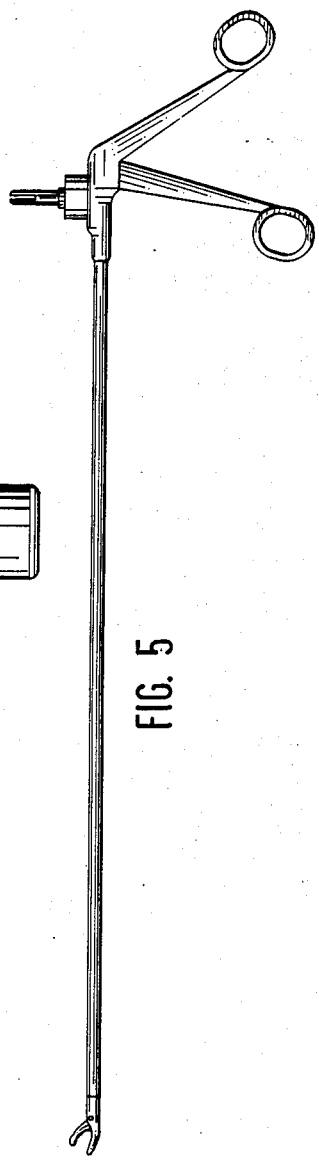
FIG. 5

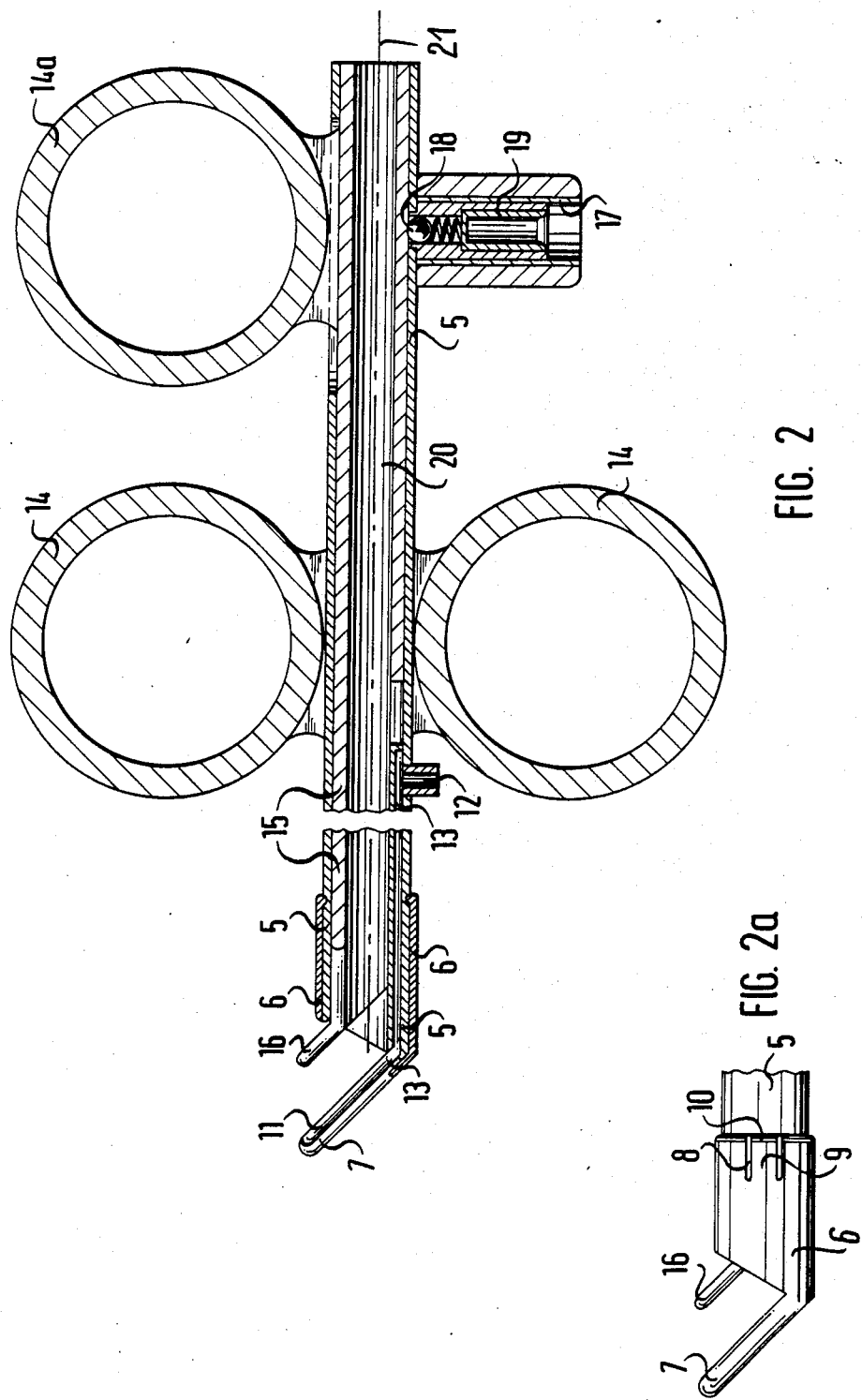

BIPOLAR COAGULATION INSTRUMENT

BACKGROUND OF THE INVENTION (i) Field of the Invention

This invention relates to a bipolar coagulation instrument.

(ii) Description of the Prior Art

A known bipolar coagulation instrument comprises two jaw members which form a forceps and which can be extended axially from the distal end of a barrel by mutually insulated HF supply means. Having grasped a piece of tissue, the jaw members can be withdrawn into the distal end of the barrel so as to press together and close, in order to allow the tissue which has been grasped to be coagulated.

Amongst other things, it is possible for known coagulation instruments to be passed through an instrument channel in a mediastinoscope to coagulate blood vessels and lymph drainage vessels. After coagulation, the known coagulation instrument has to be withdrawn and replaced by a cutting forceps to allow the piece of coagulated tissue to be severed. Hence, particularly when, for example, the oesophagus is being freed from surrounding tissue to expose it, the known coagulation instrument must be exchanged at frequent intervals for a cutting forceps and vice versa. This is a considerable strain on the doctor and a source of discomfort to the patient.

The object of the invention is to avoid this frequently repeated exchange of a coagulation instrument for a cutting forceps and vice versa in endoscopes and above all in mediastinoscopes.

SUMMARY OF THE INVENTION

With this object in view, the present invention provides a bipolar coagulation instrument suitable for use with a mediastinoscope and cutting forceps, and comprising:

(a) an outer barrel having a distal end and defining a longitudinal axis;

(b) an inner barrel situated within the outer barrel and having an internal longitudinal channel and a distal end;

(c) a first jaw member comprising two halves at the distal end of the outer barrel, the two halves being angled relative to the longitudinal axis and being spaced apart from one another;

(d) a second jaw member displaceable relative to the first jaw member along the longitudinal axis and comprising two halves at the distal end of the inner barrel, the two halves being angled relative to the longitudinal axis and being spaced apart from one another;

(e) at least one recess provided in at least one of the first and second jaw members and connected to an irrigation channel;

(f) wherein the first and second jaw members define two sets of jaw member halves, which sets are spaced apart from one another to define a gap, the gap being capable of receiving at least a part of a cutting forceps or the like passed through the channel in the inner barrel.

By means of the invention, bi-polar coagulation instrument can be passed through an instrument channel in an existing endoscope, and in particular in a mediastinoscope. Then, coagulation of blood vessels and lymph drainage vessels can be performed at two spaced points, whereupon a cutting forceps can be passed through the channel, which runs through the coagulation instrument for its full length, to sever the vessels between the two points of coagulation. At least one of the jaw members has recesses for the infeed of irrigating liquid, in order to prevent tissue or pieces of coagulated matter from adhering to the jaw members.

BRIEF DESCRIPTION OF THE DRAWINGS

In order that this invention may be more readily understood, reference will now be made, by way of example only, to the accompanying drawings in which:

FIG. 1 is a side elevation of a mediastinoscope,

FIG. 2 is an axial section through a bipolar coagulation instrument for passing through an instrument channel in the mediastinoscope, FIG. 2a is a side elevation of the distal end of the instrument shown in FIG. 2, FIG. 3 is an end elevation of said distal end, FIG. 4 is a plan view of the distal end of the instrument shown in FIG. 2, and FIG. 5 is a cutting forceps which can be passed through the channel in the coagulation instrument.

DESCRIPTION OF THE PREFERRED EMBODIMENT

The bipolar coagulation instrument shown in FIGS. 2 to 4 is suitable for extending through an instrument channel in a mediastinoscope 2 as shown in FIG. 1. the barrel of the mediastinoscope 2 also contains a bundle of optical fibres and a telescope.

The bipolar coagulation instrument shown in FIGS. 2 and 3 comprises an insulated outer barrel 5, whose distal end carries a sleeve 6 in releasably securable fashion. The sleeve 6 in turn carries halves 7a, 7b of a jaw member 7, which halves are arranged in spaced relationship to one another. The sleeve 6 is secured by, for example, providing it at its proximal end with incisions 8 parallel to its axis. The incisions 8 define resilient tongues 9 having ridges at their inner edge which engage in an annular groove 10 in the outer barrel.

The outer barrel 5 has a longitudinal axis 21.

The two halves 7a, 7b of the jaw member 7 are provided with recesses 11 to which irrigating liquid may be fed in use by a suction and irrigating pump (not shown) via a connection 12 and a passage 13.

The outer barrel 5 contains an inner barrel 15 which is axially displaceable within the outer barrel 5. To this end, the inner barrel 15 carries a gripping ring 14a which is movable within a slot provided in the outer barrel 5. The outer barrel 5 also carries gripping rings 14. The inner barrel 15 is insulated from the outer barrel 5 and, like the outer barrel 5, has at its distal end an obliquely angled jaw member 16 formed by two halves 16a 16b arranged in spaced relationship to one another. Jaw member 16 lies parallel to jaw member 7 and, like the jaw member 7, contains recesses 11 for the infeed of a liquid.

The outer and inner barrels 5 and 15 and their respective coagulating jaw members 7 and 16 are connected to an HF current source in a known manner, in which the outer barrel 5 is connected to contact 17 of a female connector and the inner barrel 15 is connected via a spring-loaded ball 18 or the like to the connector's contact 19.

The inner barrel 15 has an instrument channel 20 extending through its full length. A known cutting forceps (as shown in FIG. 5) can be passed through the channel 20 and through the gap between the two sets 7a, 16a and 7b, 16b of mutually spaced jaw member halves.

In conjunction with a mediastinoscope for example, the bipolar coagulating instrument can be used as follows. To free the oesophagus from surrounding tissue to expose it, an incision is first made on the left-hand side of the neck and through it the oesophagus is severed surgically. The oesophagus is severed similarly in the region where it enters the stomach, after the chest cavity has been opened. A probe is then passed through the oesophagus from below and the top end of the probe is connected to the folded over end of the oesophagus and traction is exerted on the probe. When this is done, the freeing of the oesophagus is performed with the cutting forceps shown in FIG. 5 which is passed through the instrument channel 20.

Blood vessels or lymph drainage vessels which are present are firstly gripped between the two pairs of mutually opposed halves 7a, 7b and 16a, 16b of the two jaw members 7 and 16 and are coagulated by applying HF current. Then the part of the vessel situated between the two halves making up each of the jaw members 7 and 16 is severed with the cutting forceps. It is thus possible for the coagulating instrument shown in FIGS. 2 to 4 and the cutting forceps shown in FIG. 5 to be used in unison under visual control through the mediastinoscope without any need for instruments to be exchanged. It is also possible for the cutting forceps to be secured in the instrument passage in the coagulating instrument in such a way as to be longitudinally displaceable, thus allowing the two devices to form a single functional unit. The withdrawal by suction of any fluid there may be in the body cavity can be performed via the suction and irrigation passage in the mediastinoscope.

We claim:

1. A bipolar coagulation instrument suitable for use with a mediastinoscope and a cutting instrument, and comprising:
    (a) an outer barrel having a distal end and defining a longitudinal axis;
    (b) an inner barrel situated within the outer barrel and having an internal longitudinal channel and a distal end;
    (c) a first jaw member comprising two halves at the distal end of the outer barrel, the two halves being angled relative to the longitudinal axis and being spaced apart from one another;
    (d) a second jaw member displaceable relative to the first jaw member along the longitudinal axis and comprising two halves at the distal end of the inner barrel, the two halves being angled relative to the longitudinal axis and being spaced apart from one another;
    (e) at least one recess provided in at least one of the first and second jaw members and connected to an irrigation channel;
    (f) wherein the first and second jaw members define two sets of jaw member halves, which sets are spaced apart from one another to define a gap, the gap being capable of receiving at least a part of the cutting instrument passed through the channel in the inner barrel.

2. An instrument according to claim 1, wherein the first jaw member is releasably secured to the distal end of the outer barrel.

3. An instrument according to claim 2, wherein the first jaw member includes a sleeve having a proximal end, which end is provided with at least one tongue defined by at least one longitudinal slot, the tongue having an internal annular ridge being releasably engaged in a complementary annular groove in the outer barrel.

* * * * *